(12) United States Patent
Schwint (10) Patent No.: US 7,632,974 B2
(45) Date of Patent: Dec. 15, 2009

(54) ALKYLATION PROCESS FOR INCREASED CONVERSION AND REDUCED CATALYST USE

(75) Inventor: Kevin J. Schwint, Long Valley, NJ (US)

(73) Assignee: Lammus Technology Inc., Bloomfield, NJ (US)

( * ) Notice: Subject to any disclaimer, the term of this patent is extended or adjusted under 35 U.S.C. 154(b) by 554 days.

(21) Appl. No.: 11/489,017

(22) Filed: Jul. 19, 2006

(65) Prior Publication Data
US 2008/0021252 A1 Jan. 24, 2008

(51) Int. Cl.
C07C 2/64 (2006.01)
(52) U.S. Cl. .............. 585/449; 58/450; 203/DIG. 6
(58) Field of Classification Search ............ 585/450, 585/449; 203/DIG. 6
See application file for complete search history.

(56) References Cited

U.S. PATENT DOCUMENTS

| | | | |
|---|---|---|---|
| 4,215,011 A | 7/1980 | Smith, Jr. | |
| 4,302,356 A | 11/1981 | Smith, Jr. | |
| 4,307,254 A | 12/1981 | Smith, Jr. | |
| 4,439,350 A | 3/1984 | Jones, Jr. | |
| 4,443,559 A | 4/1984 | Smith, Jr. | |
| 4,849,569 A | 7/1989 | Smith, Jr. | |
| 5,055,627 A | 10/1991 | Smith, Jr. et al. | |
| 5,243,115 A | 9/1993 | Smith, Jr. et al. | |
| 5,600,049 A * | 2/1997 | Sy | 585/450 |
| 5,886,736 A | 3/1999 | Chen | |
| 6,002,058 A | 12/1999 | Hearn et al. | |
| 6,620,387 B1 | 9/2003 | Sy | |
| 6,930,206 B1 | 8/2005 | Groten et al. | |
| 2004/0254412 A1 | 12/2004 | Pohl | |

FOREIGN PATENT DOCUMENTS
EP 0 410 177 1/1991

* cited by examiner

*Primary Examiner*—Thuan Dinh Dang
(74) *Attorney, Agent, or Firm*—Osha Liang LLP (57) ABSTRACT

The invention relates to a process for the production of alkylated aromatic compounds comprising introducing olefin and aromatic compounds into at least first and second vertically spaced catalytic reaction zones in an alkylation unit under alkylation reaction conditions to provide an alkylated product, wherein the second catalytic reaction zone is positioned above the first catalytic reaction zone; wherein aromatic compound from each of the at least first and second catalytic reaction zones are contacted with a cooling means for re-condensing at least a portion of the aromatic compounds vaporized from the exothermic heat of reaction of the alkylation process; and wherein the olefin is introduced into the at least first and second catalytic reaction zones via respective first and second olefin feed streams at respective olefin feed rates such as to maintain olefin partial pressures at inlets to at least first and second catalytic reaction zones which vary by less than about ten percent. The invention additionally relates to an apparatus for practicing the alkylation process of the invention.

24 Claims, 2 Drawing Sheets

ALKYLATION PROCESS FOR INCREASED CONVERSION AND REDUCED CATALYST USE

BACKGROUND OF THE INVENTION

1. Field of the Invention

The present invention relates to an improved catalytic distillation process for the production of alkylated aromatics from the alkylation reaction of olefin and aromatic compounds.

2. Description of the Related Art

The advantages of the catalytic distillation process over conventional liquid phase alkylation processes are well recognized. See, for example, U.S. Pat. Nos. 4,307,254, 4,443, 559, 4,849,569, to Smith, Jr., U.S. Pat. No. 5,243,115 to Smith, Jr. et al., and U.S. Pat. No. 4,439,350 to Jones, Jr. et al.

Some of the most common alkylation reactions include the alkylation of benzene with either ethylene or propylene to produce ethylbenzene or cumene, respectively. Ethylbenzene is particularly important for its use in the production of styrene, a precursor to polystyrene, while cumene is particularly important for its use in the production of phenol and acetone.

The catalytic distillation units thus far used are not, by themselves, capable of the complete conversion of the olefin and aromatic reactants to alkylated aromatic products. Accordingly, the catalytic distillation process typically includes an alkylation finishing reactor, operated in the liquid phase, for converting any remaining unreacted olefin and aromatic compounds to alkylated aromatic products with nearly complete conversion of the olefin. See published U.S. application Ser. No. 2004/0254412 to Pohl.

While the catalytic distillation method for alkylation reactions has provided many benefits, there remain several areas in need of improvement. For example, the process is known to suffer from a lack of reaction efficiency (i.e., impeded olefin conversion). This impedance of olefin conversion is primarily caused by an inability to control the required olefin partial pressure in the alkylation unit.

In particular, the heat of reaction (the reaction occurring in the liquid phase over the catalyst) causes partial vaporization of aromatic compounds, and a significant increase in the vapor rate from the lowermost portion of the catalyst to the uppermost portion. Gaseous olefin, flowing counter-currently upwards through the reactor, is absorbed into the liquid phase and is consumed by reaction over the catalyst. Since vapor-liquid equilibrium is approximately maintained, the result is a continuous reduction in olefin partial pressure and a corresponding decrease in liquid phase olefin concentration from the lowermost portion of the catalyst to the uppermost portion. This reduction in liquid phase olefin concentration causes correspondingly lower reaction rates and requires an ever-greater amount of catalyst to maintain the same incremental olefin conversion as it proceeds up the reactor.

Since the cost of the catalyst is typically significant, larger amounts of catalyst can result in a significant capital investment for the process. In addition, a larger amount of catalyst further exacerbates the capital and operational costs of the process by requiring a larger alkylation reactor for housing the catalyst.

Some degree of control of olefin partial pressures have been achieved in the art, but these have not resulted in maintaining satisfactory olefin conversion rates in all catalyst beds. For example, improved olefin conversion rates have been achieved throughout the catalytic distillation unit by employing an optimal benzene vapor feed rate to the bottom of the catalytic distillation unit in combination with controlling the number of olefin injection points and the flow rate to each injection point. However, even with this improvement, olefin conversion rates still drop off sharply in the middle to upper catalyst beds.

There is a need, therefore, for an improved catalytic distillation process for alkylation reactions with an improved conversion rate of the olefin. There is a particular need for improving the conversion rate of the olefin by better maintaining a desired olefin partial pressure throughout the catalyst of the catalytic distillation unit. Such an improvement would allow for the use of lesser amounts of catalyst, and consequently, a reduction in size of the alkylation reactor, and/or greater overall olefin conversion across the alkylation reactor.

SUMMARY OF THE INVENTION

These and other objectives have been achieved, firstly, by providing a process for the production of alkyl aromatic compounds in a catalytic distillation reactor, wherein variations in vapor loading and olefin partial pressures in the catalytic distillation reactor are reduced and the effective number of reaction stages can be increased. The process comprises the steps of:

introducing olefin and aromatic compounds into at least first and second vertically spaced catalytic reaction zones in an alkylation unit under alkylation reaction conditions to provide an alkylated product, wherein said second catalytic reaction zone is positioned above the first catalytic reaction zone;

wherein vaporous aromatic compounds from each of the at least first and second catalytic reaction zones are contacted with a cooling means for condensing at least a portion of said vaporous aromatic compounds;

and wherein the olefin is introduced into the at least first and second catalytic reaction zones via respective first and second olefin feed streams at respective olefin feed rates such as to maintain olefin partial pressures at inlets to at least first and second catalytic reaction zones which vary by less than about ten percent.

In a specific embodiment, the process comprises:

a) introducing one or more aromatic compounds and one or more olefins into a catalytic distillation unit having at least two lower beds, a lowermost bed, and an uppermost bed of a first alkylation catalyst, the catalytic distillation unit operated in a combination liquid phase-vapor phase mode under alkylation reaction conditions to produce a liquid alkylator bottoms effluent comprising alkylated aromatic compounds and unreacted aromatic compound discharging below the lowermost bed, and an alkylator vapor overhead stream comprising unreacted aromatic compound and unreacted olefin discharging above the uppermost bed;

b) condensing the alkylator vapor overhead stream to form a condensed alkylator overhead stream and directing said condensed alkylator overhead stream into a finishing reactor having a second alkylation catalyst and operated in a liquid phase under alkylation reaction conditions wherein the unreacted aromatic compound and unreacted olefin in the alkylator overhead stream are converted to alkylated aromatic compounds with substantially complete consumption of the unreacted olefin, thereby producing a finishing reactor effluent comprising alkylated aromatic compound and essentially no unreacted olefin;

c) removing a substantial portion of any volatile compounds in the finishing reactor effluent to form a stripped finishing reactor effluent;

d) cooling at least a portion of the finishing reactor effluent to a temperature sufficiently low for condensing at least a portion of vaporous aromatic compounds in the catalytic distillation unit, thereby forming a stripped and cooled finishing reactor effluent; and e) directing said stripped and cooled finishing reactor effluent above at least the two lower beds of the first alkylation catalyst during operation of the catalytic distillation unit.

In another embodiment, the process comprises:

a) introducing one or more aromatic compounds and one or more olefins into a catalytic distillation unit having at least two lower beds, a lowermost bed, and an uppermost bed of a first alkylation catalyst, the catalytic distillation unit operated in a combination liquid phase-vapor phase mode under alkylation reaction conditions to produce a liquid alkylator bottoms effluent comprising alkylated aromatic compounds and unreacted aromatic compound discharging below the lowermost bed and an alkylator vapor overhead stream comprising unreacted aromatic compound and unreacted olefin discharging above the uppermost bed;

b) substantially removing any alkylated aromatic compounds in the alkylator vapor overhead stream by use of a suitable absorbent capable of selectively removing alkylated aromatic compounds in the presence of unreacted aromatic compound and unreacted olefin, thereby producing a scrubbed alkylator overhead stream;

c) condensing the scrubbed alkylator overhead stream to form a condensed and scrubbed alkylator overhead stream and directing said condensed and scrubbed alkylator overhead stream into a finishing reactor having a second alkylation catalyst and operated in a liquid phase under alkylation reaction conditions wherein the unreacted aromatic compound and unreacted olefin in the scrubbed alkylator overhead stream are converted to alkylated aromatic compounds with substantially complete consumption of the unreacted olefin, thereby producing a finishing reactor effluent comprising alkylated aromatic compound and essentially no unreacted olefin;

d) removing a substantial portion of any volatile compounds in the finishing reactor effluent to form a stripped finishing reactor effluent;

e) cooling at least a portion of the stripped finishing reactor effluent to a temperature sufficiently low for condensing at least a portion of vaporous aromatic compounds in the catalytic distillation unit, thereby forming a stripped and cooled finishing reactor effluent, and f) directing said stripped and cooled finishing reactor effluent above at least the two lower beds of the first alkylation catalyst during operation of the catalytic distillation unit.

In another embodiment, the process comprises:

a) introducing one or more aromatic compounds and one or more olefins into a catalytic distillation unit having a first alkylation catalyst comprising a vertical arrangement of three to ten baled catalyst units and having a lowermost baled catalyst unit and an uppermost baled catalyst unit, the catalytic distillation unit operated in a combination liquid phase-vapor phase mode under alkylation reaction conditions to produce a liquid alkylator bottoms effluent comprising alkylated aromatic compounds and unreacted aromatic compound discharging below the lowermost baled catalyst unit and an alkylator vapor overhead stream comprising unreacted aromatic compound and unreacted olefin discharging above the uppermost baled catalyst unit, wherein olefin is fed to the first alkylation catalyst by two to seven split olefin feed lines feeding an equal number of baled catalyst units of a lower portion of said vertical arrangement of three to ten baled catalyst units, wherein the number of baled catalyst units is greater than the number of split olefin feed lines, thereby leaving an upper portion of baled catalyst units without olefin feed lines;

b) substantially removing any alkylated aromatic compounds in the alkylator overhead stream by use of a suitable absorbent capable of selectively removing alkylated aromatic compounds in the presence of unreacted aromatic compound and unreacted olefin, thereby producing a scrubbed alkylator overhead stream;

c) condensing the scrubbed alkylator overhead stream to form a condensed and scrubbed alkylator overhead stream and directing said condensed and scrubbed alkylator overhead stream into a finishing reactor having a second alkylation catalyst and operated in a liquid phase under alkylation reaction conditions wherein the unreacted aromatic compound and unreacted olefin in the scrubbed alkylator overhead stream are converted to alkylated aromatic compounds with substantially complete consumption of the unreacted olefin, thereby producing a finishing reactor effluent comprising alkylated aromatic compound and essentially no unreacted olefin;

d) removing a substantial portion of any volatile compounds in the finishing reactor effluent to form a stripped finishing reactor effluent;

e) cooling at least a portion of the stripped finishing reactor effluent to a temperature sufficiently low for condensing at least a portion of vaporous aromatic compounds in the catalytic distillation unit, thereby forming a stripped and cooled finishing reactor effluent, and f) directing said stripped and cooled finishing reactor effluent to the first alkylation catalyst during operation of the catalytic distillation unit, wherein cooled finishing reactor effluent is split into a number of split feed lines equal to or greater than the number of olefin split lines, each of the split feed lines of cooled finishing reactor effluent injecting above each of the lower portion of baled catalyst units being fed by olefin.

The invention additionally includes a catalytic distillation apparatus for achieving the process described above. In a preferred embodiment, the catalytic distillation system comprises:

a) a catalytic distillation unit having a first alkylation catalyst, an alkylator bottoms outlet below a lowermost portion of the first alkylation catalyst for discharging a liquid alkylator bottoms effluent, and an alkylator overhead outlet above an uppermost portion of the first alkylation catalyst for discharging an alkylator vapor overhead stream, wherein said catalytic distillation unit is operable in a combination liquid-vapor phase under alkylation reaction and distillation conditions;

b) means for selectively and substantially removing any alkylated aromatic compounds in the alkylator vapor overhead stream to produce a scrubbed alkylator overhead stream;

c) means for condensing and transferring said scrubbed alkylator overhead stream to a finishing reactor having a second alkylation catalyst and a finishing reactor outlet for discharging reacted finishing reactor effluent, wherein said finishing reactor is operable in a liquid phase under alkylation conditions;

d) means for cooling said finishing reactor effluent to a temperature sufficiently low for condensing at least a portion of vaporous aromatic compounds in the catalytic distillation unit; and e) means for directing cooled finishing reactor effluent into the first alkylation catalyst.

The invention advantageously controls olefin partial pressure by re-condensing the aromatics, mostly aromatic reactant (e.g., benzene) and to a lesser extent alkylated aromatics (e.g., diethylbenzene, triethylbenzene, etc.) vaporized from the exothermic heat of reaction. By re-condensing the aromatics, the flow of aromatic vapor no longer substantially increases up the alkylation column, and this in turn allows for more uniform, optimal/beneficial distribution of olefin partial pressure feed to each the catalyst beds and a more uniform counter-current vapor-liquid flow regime. Accordingly, in contrast to what has been practiced in the prior art, the olefin feed rates at each injection point are no longer required to increase up the column in order to maximize olefin partial pressure and reaction rate.

Furthermore, since the flow of aromatic vapor no longer substantially increases up the alkylator column, the initial aromatic vapor feed at the bottom of the alkylator can be significantly higher than in a prior art while maintaining or reducing the vapor loading at the top of the alkylator. A reduction in vapor loading at the top of the alkylator allows for a smaller diameter alkylator, since the hydraulic loading at the top of the alkylator is controlling.

Furthermore, a higher initial flow of aromatic vapor at the bottom of the alkylator allows for a higher initial flow of olefin at the bottom bed of the alkylator, while not exceeding any design olefin partial pressure constraints. For example, four olefin feed injections distributed, from bottom, as 18%/21%/24%/37% in a prior art process can now be four olefin injections distributed as 33%/26%/22%/19%.

The higher olefin flow to each of the lower catalyst beds (including fresh make-up olefin feed plus unreacted olefin that exits the previous bed) and resulting higher olefin conversion in each of these beds significantly increases the catalyst productivity (olefin converted per volume of catalyst) in the lower catalyst beds. This is in contrast to the lower but ever increasing flow of olefins and lower olefin conversion of the prior art.

Moreover, a reduction in alkylator diameter with the same catalyst bed height results in even higher catalyst productivity in the lower catalyst beds since olefin conversion increases and catalyst volume decreases. The resulting higher catalyst productivity has no negative consequences because catalyst productivity in both cases is sufficiently low so as not to be a significant factor in catalyst run-length or life expectancy.

The amount of olefin converted across the lower beds (i.e., those beds that receive fresh make-up olefin feed) is now significantly higher than the prior art. For example, the olefin converted across the lower four catalyst beds in a prior art process is typically 70% of the total olefin feed. This is in contrast to the present invention wherein olefin conversion is typically at least 72% of the total olefin feed, but with 40% less catalyst.

The upper catalyst beds (i.e., those beds that do not receive fresh make-up olefin feed) also perform better. These catalyst beds further react un-converted olefin exiting the lower beds so that the overall CD alkylator olefin conversion is at least 75-80% (when a finishing reactor is employed), and provide an allowance for run-length (catalyst ageing). First, the partial pressure of olefin is higher, even without the injection of fresh make-up olefin feed, because of the condensation of vaporized aromatics, compared with the prior art process. Second, there is now less unconverted olefin from the lower catalyst beds entering the upper catalyst beds compared with the prior art process. Third, for the same amount of total catalyst and smaller diameter alkylator, there is less catalyst contained in the lower beds, and thus more catalyst contained in the upper beds, compared with the prior art process. This means there are now a greater number of upper catalyst beds of the same bed height, and thus a greater total upper bed height available to contact and convert the olefin.

The improved lower catalyst bed operation and improved upper catalyst bed operation results in significantly higher olefin conversion in the alkylator with the same amount of catalyst compared with the prior art process (5% to 15% higher alkylator conversion, depending on the design run-length); or significantly less catalyst (30% to 40% less catalyst, depending on run-length catalyst allowance) required to achieve the same olefin conversion as compared with the prior art process.

The higher olefin conversion of the present invention allows for a smaller finishing reactor and less finishing reactor catalyst than the prior art since less olefin needs to be converted in the finishing reactor. If the olefin conversion of the present invention is approximately the same as compared with prior art processes, this would still allow for a smaller alkylator and less alkylator catalyst. Either case provides economic benefits.

Furthermore, since there can be more total catalyst beds in a smaller diameter alkylator having the same amount of total catalyst, in contrast to what has been practiced in the prior art, there can now be more injection points to distribute the olefin feed amongst additional catalyst bed. For example, four olefin feed injections distributed (from bottom) as 18%/21%/24%/37% in a prior art process can now be five olefin injections distributed as 28%/23%/19%/16%/14%.

The more uniform distribution of olefin to more catalyst beds means: 1) more beds receive fresh make-up olefin feed and operate at high productivity; and 2) there are more beds operating at maximum olefin partial pressure. This effectively increases the number of reaction stages. The greater distribution of olefin feed and lower catalyst bed productivity can also result in more uniform catalyst aging and potentially longer catalyst run length.

More CD alkylator beds at maximum olefin partial pressure results in still higher conversion rates and lower required finishing reactor conversion. Overall, the average olefin partial pressure throughout the catalytic distillation unit is higher in the present invention, and therefore, the average reaction rate throughout the catalytic distillation unit is higher.

In a particularly preferred embodiment, the invention provides the above advantages by including a process for cooling the effluent from a finishing reactor and feeding the cooled finishing reactor effluent to the alkylation catalyst during an alkylation reaction. The cooled finishing reactor effluent advantageously helps maintain a desired olefin partial pressure in the alkylation catalyst by effecting a reduction in the vapor pressure of the aromatic by condensation of the aromatic. The process allows for an improved conversion of olefin (e.g., 90% instead of 80%) and/or a reduction in the amount of required catalyst and a reduction in the size of the alkylation and/or finishing reactor. These improvements also allow for a reduction in costs and better product yields for the process.

BRIEF DESCRIPTION OF THE DRAWINGS

Various embodiments are described herein with reference to the drawings wherein.

DETAILED DESCRIPTION OF PREFERRED EMBODIMENTS

As used herein, the term "aromatic" includes non-alkyl group-containing aromatic compounds, such as benzene and naphthalene, as well as alkyl-containing aromatic compounds, such as toluene, xylene, and the like. The term "alkylated aromatic" refers to compounds to which one or more additional alkyl groups are attached by the aromatic alkylation process described below.

Figure 1:
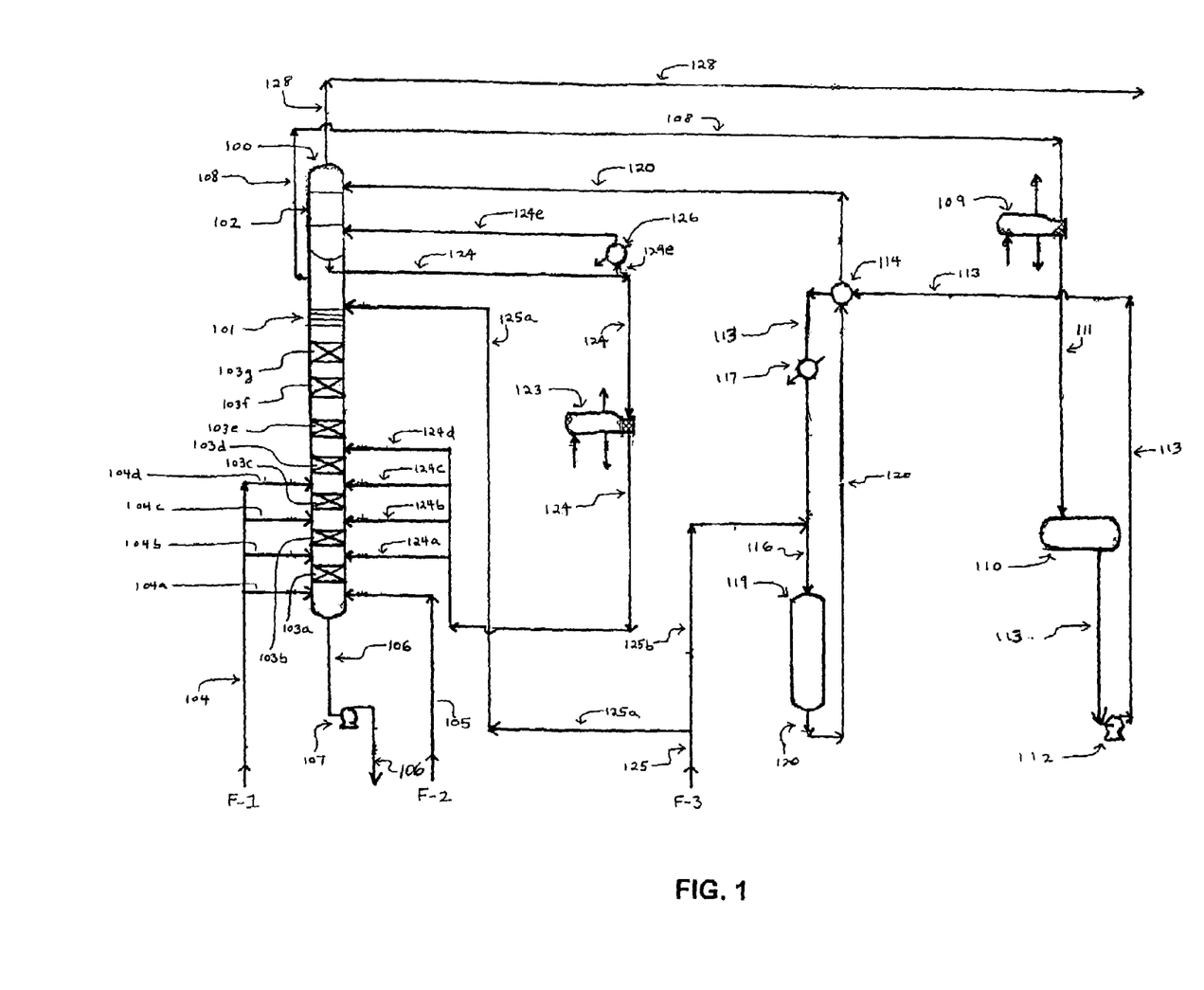
FIG. 1 is a view of a preferred catalytic distillation process of the invention; and, FIG. 2 is a view of a preferred distillation system coupled to element 106 carrying the alkylator bottoms streamline.

Referring to FIG. 1, the process of the invention requires an alkylation unit corresponding to element 100, as shown. In the alkylation unit, one or more olefin compounds and one or more aromatic compounds are introduced into at least two (i.e., first and second) vertically spaced catalytic reaction zones under alkylation reaction conditions, wherein the second catalytic reaction zone is positioned above the first catalytic reaction zone. During operation of the alkylation unit, the olefin and aromatic compounds react on contact with the catalyst in each of the reaction zones to produce one or more alkylated aromatic compounds.

The alkylation unit 100 is typically a catalytic distillation unit that operates in a combination liquid phase-vapor phase mode and under suitable alkylation reaction conditions, as known in the art. Preferably, the catalytic distillation unit 100 is operated at a pressure of from about 270 psig to about 550 psig and a temperature of from about 365° F. to about 482° F. (185° C. to about 250° C.), with an aromatics to olefin weight ratio in the preferred range of about 2.0 to about 3.5. A prior known catalytic distillation unit has been previously described in detail in U.S. Pat. No. 4,849,569 to Smith, Jr.

The alkylation catalyst can be any suitable alkylation catalyst known in the art. The preferred compositions and forms of such alkylation catalysts have been previously described in detail in U.S. Pat. Nos. 4,849,569 and 4,443,559 to Smith, Jr., both of which are incorporated herein by reference in their entirety. A suitable alkylation catalyst, besides having the ability to catalyze an alkylation reaction, should have an appropriate surface area and allow vapor to flow through it, as described in U.S. Pat. Nos. 5,243,115 to Smith Jr., et al., and U.S. Pat. Nos. 4,215,011 and 4,302,356 to Smith Jr., all of which are incorporated by reference herein in their entirety.

The alkylation catalyst is preferably a suitable acidic catalyst. Suitable acidic catalysts include molecular sieves (mole sieves) and cation exchange resins, as described in the patent references cited above. Some particularly preferred catalysts include zeolite X, zeolite Y, zeolite L, TMA Offretite, mordenite, amorphous silica-alumina, zeolite BEA (beta), zeolite MWW, MFI catalyst, and zeolite BEA.

Preferably, the alkylation catalyst is in the form of discrete catalyst beds. In a preferred embodiment, the catalyst beds are in the form of packaged (i.e., baled) catalyst units vertically arranged in the catalytic distillation unit. More preferably, an appropriate spacing is provided between each of the vertically arranged baled catalyst units. For example, in a particularly preferred embodiment, the alkylation catalyst contains a plurality of vertically arranged baled catalyst units wherein each baled catalyst unit is limited to approximately six feet in height with a spacing of 18 to 30 inches.

In a particular embodiment, the alkylation catalyst comprises at least two, more preferably three, and more preferably four baled catalyst units in a vertical arrangement. In another embodiment, the alkylation catalyst comprises five to ten baled catalyst units in a vertical arrangement. For example, the alkylation catalyst can comprise a vertical arrangement of five, more preferably six, and even more preferably, as shown in FIG. 1 (i.e., elements 103a-103g), seven baled catalyst units having some spacing between each baled catalyst unit.

The process described above preferably further comprises a finishing reactor 119. The finishing reactor reacts unreacted aromatic compound and unreacted olefin compound from the alkylator overhead stream to alkylated aromatic compounds in a highly efficient liquid phase process which allows for the substantially complete consumption of unreacted olefin. Accordingly, essentially no unreacted olefin remains after the finishing process.

Since the finishing reactor operates more efficiently than alkylation in the mixed vapor-liquid phases of the catalytic distillation unit, the finishing reactor typically requires less catalyst than the catalytic distillation unit. Finishing reactor 119 preferably operates at a temperature of from about 392° F. to about 446° F. (200° C. to about 230° C.), a pressure of from about 550 psig to about 900 psig, and an aromatics to olefin mole ratio of from about 2.0 to about 10.0.

The alkylation catalyst of the finishing reactor can be the same or different (compositionally and/or in physical design) than the alkylation catalyst of the alkylation unit. In order to distinguish the two alkylation catalysts where a finishing reactor is used, the alkylation catalyst of the alkylation unit will hereinafter be referred to as the "first alkylation catalyst" and the alkylation catalyst of the finishing reactor as the "second alkylation catalyst."

Whereas the the first alkylation catalyst is preferably in the form of packaged bales, the second alkylation catalyst is preferably in the form of a fixed bed of loose catalyst having any of the suitable compositions for alkylation catalysts as described above for the first alkylation catalyst. The composition of the second alkylation catalyst is more preferably selected from zeolite Y, zeolite BEA (beta), zeolite MWW, Mordenite, or MFI catalyst.

According to the invention, vaporous aromatic compounds from each of the at least first and second catalytic reaction zones is contacted with cooling means for condensing at least a portion of the vaporous aromatic compounds. Any means known in the art for cooling can be used for the cooling means. For example, the cooling means can be a cooling element to indirectly remove heat from the catalytic distillation unit to a colder process stream or utility.

Some examples of cooling elements include any of the suitable coolers or heat exchangers known in the art. Some more specific examples of cooling elements include pump-around coolers and bayonette-type U-tube heat exchangers (e.g., with the coolant on the tube side) inserted between the catalyst beds and external shell-and-tube heat exchangers where the alkylator inter-bed mixture is forced to circulate through the tube side of the heat exchanger (e.g., with the coolant on the shell side).

The cooling means can also be a cooled aromatic-containing stream which is preferably at a temperature sufficiently low for the condensation, more preferably re-condensation, of at least a portion, more preferably a major portion, of the vaporized aromatic compounds. For example, a cooled aromatics stream from feed source F-3 could be used for condensing vaporous aromatics in the catalytic distillation unit, either in place of or in addition to the cooled finishing reactor effluent.

More preferably, the cooling means is cooled effluent from a finishing reactor. For example, in a preferred embodiment, cooling is accomplished by first stripping the finishing reactor effluent of volatile compounds (e.g., in a lights stripper 102) before cooling the finishing reactor effluent, and then directing the stripped and cooled finishing reactor effluent above at least two lower catalyst beds.

The cooled finishing reactor effluent advantageously helps maintain a desired olefin partial pressure in the alkylation catalyst by effecting a reduction in the vapor pressure of the aromatic by re-condensation of at least a major portion (e.g., equal to or greater than 90%) of the aromatics vaporized from the exothermic heat of reaction. The improvement allows for an improved conversion rate of the olefin in the process, which allows for, inter alia, a reduction in the amount of required catalyst and a reduction in the size of the alkylation reactor. These improvements allow for a reduction in costs and better product yields for the process.

The first alkylation catalyst is preferably located in the vicinity of the lower portion of the catalytic distillation unit 100. More preferably, a sufficient space is provided below the lowermost portion of the first alkylation catalyst for the introduction and accumulation of aromatic and/or olefinic vapors or liquids. Similarly, it is preferred that the catalytic distillation unit 100 include a sufficient space above the uppermost portion of the first alkylation catalyst for inclusion of an absorbent (e.g., 101) and/or a lights stripper (e.g., 102), each of which are described in further detail below. A space below the lowermost and/or above the uppermost portions of the first alkylation catalyst can range from, for example, one-twentieth to one-half the height of the alkylation unit. This range is given for purposes of illustration and is not to be construed as a limitation of the scope of the invention. Values outside of this range can be used where appropriate.

An olefin feed F-1 and an aromatics feed F-2 are introduced into at least first and second catalytic reaction zones of an alkylation unit by suitable olefin and aromatics feed lines (i.e., olefin-containing and aromatic-containing streams). Each feed line can be independently split or unsplit and connected to the alkylation unit directly or indirectly to bring the olefin or aromatics feed in contact with (i.e., into) the alkylation catalyst. The olefin feed and aromatics feed can be introduced into the alkylation unit separately in the form of separate olefin and aromatic feed lines, or alternatively, as a combined olefin-aromatics mixture in one or more feed lines.

In one embodiment, olefin is fed to the first alkylation catalyst at two or more locations of the catalyst by use of two or more streams of olefin. For example, the olefin feed line can be split into two to ten, or four to eight split olefin feed lines, either of which feed into a vertical arrangement of two to ten or four to eight baled catalyst units of the first alkylation catalyst, respectively. Preferably, each olefin feed line directs olefin to (and more preferably below) a single baled catalyst unit. The number of split olefin feed lines and number of baled catalyst units are independent of each other provided that there are at least as many baled catalyst units as there are olefin feed lines.

For example, in a preferred embodiment, as shown in FIG. 1, olefin feed F-1 is sent to the first alkylation catalyst via an olefin feed line 104, which is split into four streams 104a-104d, each of which feeds olefin to each of four baled catalyst units (i.e., 103a-d) of a total of seven vertically arranged baled catalyst units (i.e., 103a-g). If desired, the olefin feed line 104 can be divided into five, six, seven, or a higher number of olefin streams, each of which directs olefin to a baled catalyst unit and wherein there are at least five, six, seven, or a higher number of vertically arranged baled catalyst units.

Preferably, olefin is injected into a lower portion of catalyst beds, thereby leaving one or more (e.g., 1, 2, 3, or 4) catalyst beds of an upper portion of catalyst beds without direct olefin feed. The olefin is more preferably injected below each catalyst bed of the lower portion of catalyst beds. Having catalyst beds above the uppermost olefin feed point is particularly advantageous in that these upper catalyst beds react the olefin remaining from the catalyst bed above the uppermost source of olefin feed.

For example, in a particular embodiment, olefin is fed to the first alkylation catalyst by two to seven split olefin feed lines feeding an equal number of baled catalyst units of a lower portion of a vertical arrangement of three to ten baled catalyst units of the first alkylation catalyst, wherein the number of baled catalyst units is greater than the number of split olefin feed lines, thereby leaving an upper portion of baled catalyst units without olefin feed lines.

In another embodiment, olefin is fed to the first alkylation catalyst by three to five split olefin feed lines feeding an equal number of baled catalyst units of a lower portion of a vertical arrangement of four to eight baled catalyst units of the first alkylation catalyst, wherein the number of baled catalyst units is greater than the number of split olefin feed lines, thereby leaving an upper portion of baled catalyst units without olefin feed lines.

In the vicinity of where each olefin and aromatic feed line meets the catalytic distillation unit 100, means are provided for the olefin or aromatic to be distributed onto (or into) the catalyst. The means for distributing the olefin or aromatic can be any suitable means known in the art, such as sparging or spraying.

The one or more aromatic compounds in aromatic feed line F-2 are preferably introduced via a single feed line 105 into the catalytic distillation unit at any suitable location thereon. In a preferred embodiment, as shown in FIG. 1, the aromatic feed F-2 is introduced below the lowermost portion of the first alkylation catalyst, e.g., below baled catalyst unit 103a.

The olefin feed in F-1 and the aromatic feed in F-2 can be introduced independently in a liquid or vapor form. The aromatics are preferably introduced into the lowermost portion of the catalytic distillation unit 100 below the baled catalyst unit 103a. The gaseous olefin is distributed and dissolved in the liquid phase of the aromatic compound. The catalyst is wetted in the liquid phase and the alkylation reaction takes place in the liquid phase on the catalyst surface.

The olefin feed can contain any suitable concentration of olefin. For example, the olefin can be in a low concentration, e.g., 5%, 10%, 15%, or 20% by volume, weight, or mole ratio, or a moderate concentration, e.g., 25%, 35%, 40%, 50%, or 60%. However, the present invention is especially advantageous for higher concentration of olefin feeds, e.g., 70%, 80%, 90%, 95%, 98%, or higher by volume, weight, or mole ratio.

The source of olefin can be any suitable source. For example, the olefin can be of high purity, such as polymer grade ethylene or propylene. Alternatively, the olefin can be less pure, such as from an offgas from a refinery operation, e.g., from a fluid catalytic cracking (FCC) operation. An offgas source of ethylene can contain, for example, approximately 10% to about 30% by volume of ethylene and approximately 50% to 70% methane and hydrogen, as well as minor amounts of other light hydrocarbon components, such as ethane and propane. Other light components can include carbon monoxide, carbon dioxide, and/or nitrogen.

The olefin introduced via olefin feed line 104 needs to be capable of undergoing an alkylation reaction with one or more aromatic compounds according to the process of the invention. For example, the olefin can be one or more hydrocarbon compounds having two to twenty carbon atoms and at least one double bond. Some examples of suitable olefins include ethylene, propylene, 1-butene, 1,3-butadiene, 2-butene, 1-pentene, 1-hexene, 2-hexene, 3-hexene, 1-heptene, 1-octene, 1-nonene, 1-decene, ethylbenzene, styrene, and the divinylbenzenes.

Ethylene and propylene are among the most significant olefins according to the present invention since they can be alkylated with benzene to make at least two commercially important endproducts, ethylbenzene and cumene, respectively.

The one or more aromatic compounds introduced via aromatics feed line 105 need to be capable of undergoing an alkylation reaction (i.e., alkylatable) with one or more olefin compounds according to the process of the invention. Some examples of suitable alkylatable aromatic compounds useful as feed components in the process described herein include benzene, toluene, the xylenes (e.g., o-, m-, and p-xylene), naphthalene, biphenyl, and their derivatives. Benzene is particularly preferred.

The olefin, once contacted with the aromatic compound in the presence of the first alkylation catalyst, reacts with the aromatic compound to form alkylated aromatic compounds, e.g., monoalkylated aromatic compound (e.g., ethylbenzene or cumene) along with a portion of polyalkylated aromatic compounds. The monoalkylated aromatic compound is typically the desired product.

Alkylator bottoms effluent 106, which preferably discharges below the lowermost portion of the first alkylation catalyst, includes these alkylated aromatic products along with some unreacted aromatic, such as unreacted benzene. The alkylated aromatic products from alkylator bottoms effluent 106 can be separated from each other and from unreacted aromatic according to any suitable processes known in the art, such as by distillation, as further discussed below.

The components discharged above the uppermost portion of the first alkylation catalyst (e.g., above baled catalyst unit 103g and into alkylator overhead stream 108) include, inter alia, unreacted aromatic, unreacted olefin, and typically, an amount of alkylated aromatic compounds. Alkylated aromatics, if not excluded from the alkylator overhead stream 108, will react in the finishing reactor 119 with olefins to produce polyalkylated aromatics. Accordingly, when maximizing selectivity to monoalkylated product is desired, it is preferable that such alkylated aromatic compounds be substantially excluded from alkylator overhead stream 108 prior to processing the alkylator overhead stream in the finishing reactor 119, by, for example, use of a suitable absorbent 101 preferably positioned above the uppermost portion of the first alkylation catalyst and below where the alkylator overhead stream is discharged.

The absorbent 101 is capable of selectively removing alkylated aromatic compounds in the presence of unreacted aromatic and olefin compounds, and preferably includes a trayed or packed section capable of providing at least about two to three theoretical stages of removal with the aid of a suitable absorbent. Preferably, the absorbent is a liquid aromatic which absorbs the alkylated aromatic compound. The liquid aromatic is preferably introduced into the upper portion of the absorbent 101 via line 125a in order to produce a downward flow of the liquid aromatic against the components exiting the uppermost catalyst bed 103g.

Figure 2:
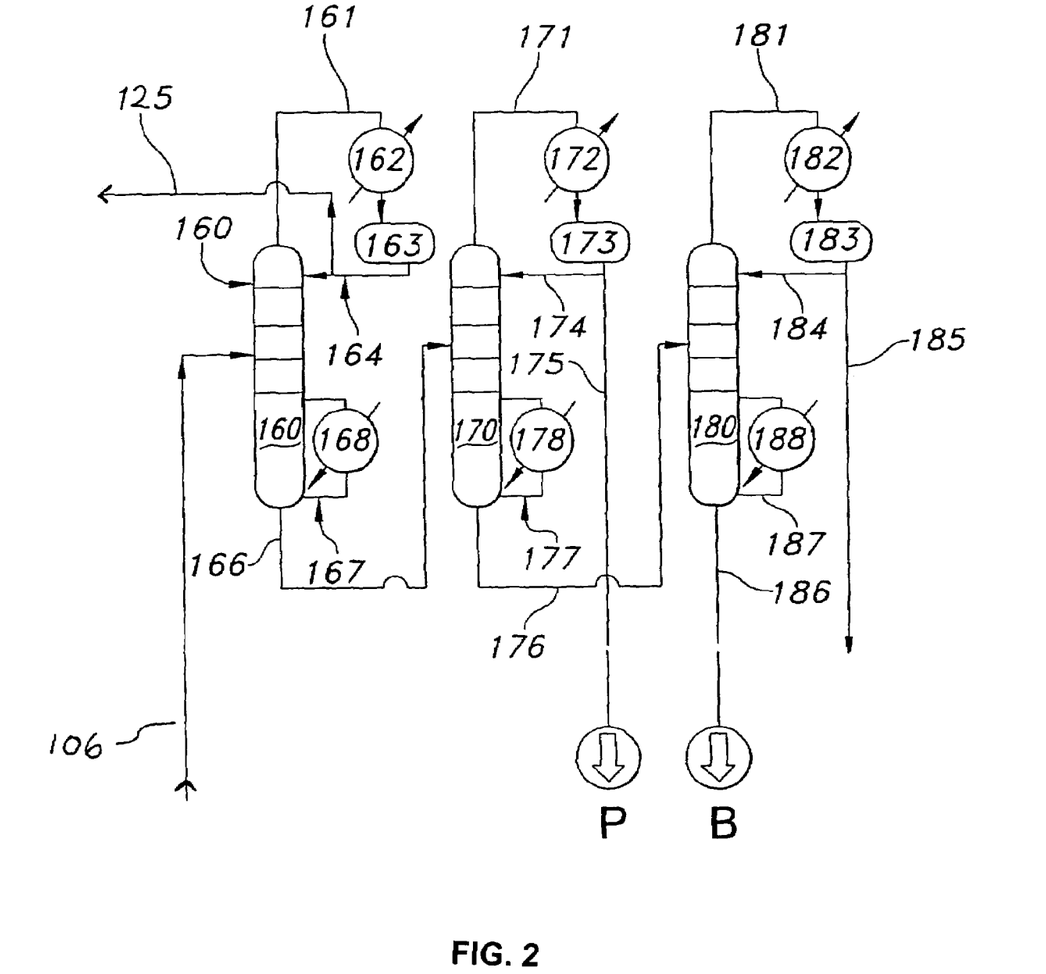

The source of the liquid aromatic absorbent, i.e., liquid aromatics feed line 125a, is preferably split from a main liquid aromatics feed line 125, which is connected to a liquid aromatics feed source F-3. The liquid aromatics source can be recycled aromatic (e.g., recycled benzene) recovered from alkylator bottoms effluent 106 by use of an appropriate distillation system, such as shown in FIG. 2, as described below. More preferably, the absorbent is fresh aromatic reactant, e.g., fresh benzene, since a fresh aromatic source will contain little or no alkylated aromatic compounds, and will thus, more efficiently remove the alkylated aromatics.

In a preferred embodiment, before being fed into the finishing reactor 119 via stream line 116, the alkylator overhead stream 108, now substantially removed of alkylated aromatics and containing non-alkylated aromatics, olefin, and light components, is condensed or sub-cooled (more preferably not sub-cooled) in one or more cooling elements 109 capable of condensing and/or subcooling the overhead stream 108. The condensed unreacted olefin/aromatics stream line 111 is then accumulated into a finishing reactor feed drum 110, discharged via a feed drum discharge line 113 to one or more finishing reactor feed pumps 112, and pumped through a finishing reactor feed pump discharge line 113 to a heat exchanger 114 where the condensed alkylator overhead stream is pre-heated by finishing reactor effluent line 120. The preheated alkylator overhead stream is then fed from heat exchanger 114 via line 113 to finishing reactor feed heater 117 for further heating. Liquid aromatics from source F-3 are then combined with the heated finishing reactor feed via split feed line 125b (preferably containing fresh and/or recycled benzene) to control the aromatic to olefin ratio, thereafter forming the finishing reactor inlet stream 116 which contains heated unreacted olefin and aromatics from the alkylator overhead stream as well as additional liquid aromatic from line 125b, and optionally, some lights.

The finishing reactor effluent stream 120 includes, predominantly, monoalkylated aromatic, polyalkylated aromatic, and unreacted aromatic compounds, along with gaseous components (i.e., lights), which includes such gaseous species as methane, ethane, hydrogen, carbon monoxide, carbon dioxide, propane and/or nitrogen. In a preferred embodiment, at least a portion of the finishing reactor effluent stream 120 is first cooled (e.g., by cooled stream line 113 in exchanger 114, as shown in FIG. 1), preferably to its bubble point temperature corresponding to the pressure top of the stripper, before being processed in a lights stripping zone 102. The lights stripping zone includes at least one lights stripper, which can be any suitable lights stripper known in the art, capable of selectively removing gaseous components, as described above, from the finishing reactor effluent 120.

Preferably, the lights stripping zone 102 is housed in the uppermost portion of the catalytic distillation unit, and preferably includes one to five trays, and more preferably, two to four trays. If found necessary or desired, the finishing reactor effluent can also be separately removed of ethane by use of a de-ethanizer, as known in the art. The separated lights in the lights stripping zone 102 can be released as overheads through the vent line 128. If desired, the lights can be condensed and sent to an accumulator. The light stripping zone 102 can also stand alone along with suitable bottoms pumps.

The stripped finishing reactor effluent stream 124 is received as bottoms from the lights stripper 102. To further optimize the stripping process, a portion of the stripped finishing reactor effluent stream 124 is preferably heated in a lights stripper reboiler 126 and recirculated into the lights stripper 102 via split line 124e.

In prior art processes, it is typical for uncooled and unstripped finishing reactor effluent to be sent back to the top of the catalytic distillation unit above the uppermost catalyst bed as reflux to provide downward liquid traffic in the unit. However, unlike what is known in the prior art, the present invention provides a process whereby finishing reactor effluent 124 is stripped of lights in the stripper 102 and then cooled, and more preferably sub-cooled, by cooler(s) 123 before being divided amongst the beds (preferably, the lower beds) of the first alkylation catalyst. Preferably, cooled stream 124 is divided in approximately equal parts amongst the lower beds of the first alkylation catalyst to which olefin is being fed, and more preferably, above each bed of the lower beds of the first alkylation catalyst. The cooled stream 124 is more preferably injected between the catalyst beds, preferably using an internal pipe distributor such as a "ladder type" liquid pipe distributor.

The stream 124 is cooled to a temperature sufficiently low for condensing at least a portion of vaporous aromatic vapor in the catalytic distillation unit. Preferably, the stream 124 is cooled to a temperature sufficiently low to re-condense at least a major portion of the aromatic compounds vaporized by the heat of reaction in the catalytic distillation unit, wherein a "major portion" is preferably at least approximately ninety percent of the aromatic compounds vaporized in the catalyst bed.

More preferably, the cooled stream 124 is cooled to a temperature that would result in condensing the same amount of aromatic that is vaporized in the catalyst bed below which it is fed. Typically, the stream would be cooled against boiler feed water (BFW) generating low pressure (LP) or medium pressure (MP) steam, which could result in stream temperatures anywhere from 250° F. to 350° F., depending on steam levels. Heat integration, in which the stream is exchanged with other process streams is also possible. In fact, since the temperature at the point in the catalytic distillation unit at which cooled liquid is fed is typically in the range of 365° F. to 482° F., a liquid having a temperature within or below the foregoing temperature range will result in condensing vapor in the alkylator.

For example, in a preferred embodiment, the stripped and cooled finishing reactor effluent is introduced into the catalytic distillation unit at a temperature of about 289° F., based on an 18° F. approach to the LP steam temperature of 271° F. This will typically result in an alkylator bottoms temperature (106 stream) of about 430° F. to about 436° F.

The cooled finishing reactor effluent stream re-condenses aromatic vapor (e.g., benzene vapor) that was generated by the heat of reaction produced in the first alkylation catalyst. As a result of the condensation of aromatic, desired olefin partial pressures are more easily maintained and olefin is more evenly distributed throughout the first alkylation catalyst, and particularly, at the inlet to at least the first and second catalytic reaction zones.

The equalization of olefin partial pressures is particularly important for the lower portion of catalyst beds in the first alkylation catalyst to which olefin is being fed. The catalyst beds in the upper portion of the first alkylation catalyst which do not have a direct feed of olefin are subject to olefin partial pressures which continue to decline in the direction of the uppermost catalyst bed.

For example, in a preferred embodiment, the variation in olefin partial pressures at the inlets of lower catalyst beds being fed olefin does not exceed about ten percent. More preferably, the variation in olefin partial pressures at the inlets of lower catalyst beds does not exceed about five percent, and even more preferably, about one percent. In a particularly preferred embodiment, the variation in olefin partial pressures is essentially absent, i.e., less than one percent, in the lower portion of catalyst beds (e.g., in olefin feed streams 104a-104d), and the olefin partial pressures in the lower portion of catalyst beds are essentially equal with a maximum allowable partial pressure of about 3.5 bar.

In contrast to prior art processes which require successively greater olefin feed rates to maintain maximum olefin partial pressure at increasingly higher catalyst beds in the catalytic distillation column, the process of the present invention can maintain maximum olefin partial pressure with approximately the same olefin feed rates in olefin feed streams (e.g., 104a-104d), which are successively higher in position in the catalytic distillation column. For example, the olefin feed rate of an olefin feed stream of a second catalytic reaction zone (e.g., 104b), can be approximately the same as the olefin feed rate of an olefin feed stream of a first catalytic reaction zone (e.g., 104a), which is positioned below 104b of the second catalytic reaction zone. Likewise, the olefin feed rate of olefin feed stream 104c can be approximately the same as the olefin feed rate of olefin feed stream 104b, which is at a position in the catalystic distillation column below 104c, and so on, for olefin feeds successively higher up in the column.

Moreover, the olefin feed streams at higher positions in the column can have olefin feed rates which are lower than the olefin feed rates of olefin feed streams which are at lower positions in the catalytic distillation column. For example, the olefin feed rate of 104a can be one to five percent lower for 104a as compared to 104b, 104c, or 104d.

Since the improvement allows catalyst efficiency to be maintained at a high level, olefin can be fed at higher rates to the catalyst without substantial loss of conversion. Accordingly, the improvement allows for the use of less catalyst as compared to processes known in the prior art.

Preferably, the stripped and cooled finishing reactor effluent stream 124 is fed to the first alkylation catalyst at two or more locations by use of two or more split feed lines from stream 124. More preferably, stream 124 is split into two to ten and more preferably four to eight split feed lines which feed into a vertical arrangement of two to ten, and more preferably four to eight baled catalyst units of the first alkylation catalyst. Each split stream of cooled finishing reactor effluent is directed to (and more preferably above) at least one baled catalyst unit, and the number of split feed lines and number of baled catalyst units are independent of each other, provided there are at least as many baled catalyst units as there are split feed lines of cooled finishing reactor effluent.

In a preferred embodiment, the cooled finishing reactor effluent stream is injected via separate streams to only those catalyst beds in the lower portion of the first alkylation catalyst to which olefin feed is being injected. For example, as shown in FIG. 1, cooled finishing reactor effluent is sent to the first alkylation catalyst via stream 124, which is split into four streams 124a-124d, each of which feeds cooled finishing reactor effluent to each of four baled catalyst units (i.e., 103a-d) in a lower portion of the catalyst beds to which olefin feed is being injected, out of a total of seven vertically arranged baled catalyst units (i.e., 103a-g) in the catalytic distillation unit 100. If desired, the cooled finishing reactor effluent 124 can be divided into five, six, seven, or a higher number of streams, each of which is fed to a baled catalyst unit and wherein there are at least five, six, seven, or a higher number of vertically arranged baled catalyst units.

It may also be preferred in some embodiments to inject the cooled stream 124 above the catalyst beds to which no olefin is being fed. In the upper portion of catalyst beds in which no olefin is being fed, there is still unreacted olefin present in ever decreasing amounts along with an ever decreasing reaction rate, as the uppermost catalyst bed is approached. Nevertheless, condensing of the aromatic in these upper catalyst beds has the benefit of increasing the partial pressure of the unreacted olefin, and thus, serves to increase reaction rates above what they would be if there were no condensation of aromatics in these catalyst beds.

Any number of complementary or auxiliary components can be included in the process described above for the modification, enhancement, or optimization of the process. For example, in a preferred embodiment, the alkylator bottoms effluent 106 is further processed via a suitable distillation process to separate one or more of the products in the alkylator bottoms effluent (e.g., monoalkylated or polyalkylated aromatics) from other components of the alkylator bottoms effluent, as well as to recover unreacted aromatic (e.g., recycled benzene).

A preferred distillation system is shown in FIG. 2. Referring to FIG. 2, the alkylator bottoms effluent 106 is preferably first fed via pump 107 to distillation column 160 of the distillation unit shown. Column 160 separates unreacted aromatic from monoalkylaromatic and heavier components. For example, column 160 can separate benzene from ethylbenzene and heavier components. The aromatic is distilled overhead as a vapor and is preferably liquified by being sent via line 161 to condenser 162. The liquified aromatic can then be held in an accumulator 163, if desired. Liquified aromatic from accumulator 163 can then be sent via line 164 back to column 160 as a reflux. A portion of the aromatic can be drawn off from line 164 as liquid aromatic feed line 125 (as also shown in FIG. 1) and sent back to the alkylator 100 via split line 125a either directly or through any preferred intermediary steps. Bottom stream 167 is preferably recirculated back to the column 160 through reboiler 168.

A bottom stream 166 from column 160 is preferably sent to distillation column 170 for separation of the monoalkylaromatic component from the polyalkylaromatics component. The monoalkylaromatic can include, for example, ethylbenzene or cumene. The polyalkylaromatics can include, for example, diethylbenzenes, triethylbenzenes, tetraethylbenzenes, di-n-propylbenzenes, ethyl-n-propylbenzenes, ethylisopropylbenzenes, diisopropylbenzenes, and triisopropylbenzenes. Bottom stream 177 is preferably recirculated back to distillation column 170 through reboiler 178.

The overhead monoalkylaromatic vapor stream 171 from column 170 is preferably liquified in condenser 172 and sent to accumulator 173. A portion of the overhead is preferably returned to column 170 as reflux via line 174. Another portion of the overhead 171 is preferably withdrawn via line 175 as monoalkylated aromatic (e.g., ethylbenzene or cumene) product P.

Bottom stream 176 containing polyalkylated aromatics is preferably further processed by distillation column 180 for separation of polyalkylaromatic (e.g., diethyl benzene), as overhead stream 181, from flux oil (B), as bottom stream 186. Flux oil typically contains diphenylethane, tetraethylbenzene, and other high boiling components, and can be discarded or used, e.g., as a heat transfer fluid, fuel oil or an absorbent.

The bottom stream 187 is preferably recirculated back to column 180 through reboiler 188. A portion of the bottoms from distillation column 180 can be withdrawn via line 186 as the flux oil B. The overhead polyalkylated aromatics vapor stream 181 is preferably liquified in condenser 182 and sent to accumulator 183. A portion of the overhead can be returned to column 180 via line 184 as a reflux.

In a further embodiment, a transalkylator can be included in the process. A transalkylator reacts polyalkylated aromatic product with non-alkylated aromatic to produce, predominantly, monoalkylated product. For example, a transalkylator can be included in the process to react diethylbenzene and benzene to obtain ethylbenzene as the predominant product. To accomplish this, the polyalkylated aromatics stream 185 can be directly fed into a transalkylator, or indirectly fed through, for example, one or more vent strippers or vent absorbers.

The transalkylator contains a suitable transalkylation catalyst such as zeolite beta, zeolite Y or other suitable zeolite, and is operated under suitable transalkylation reaction conditions known in the art. For example, the transalkylator can be operated in a temperature of from 365° F. to about 482° F.

(185° C. to about 250° C.), a pressure of from about 350 psig to about 600 psig, a space velocity of from about 3.5 to 5.0 WHSV, and a molar ratio of phenyl to ethyl of from about 2.0 to about 5.0, wherein 3.0 is preferred.

In another aspect, the invention is directed to an apparatus for practicing any of the alkylation processes described above. The apparatus preferably comprises: a) a catalytic distillation unit having a first alkylation catalyst, as described above, b) means for selectively and substantially removing any alkylated aromatic compounds in the alkylator vapor overhead stream to produce a scrubbed alkylator overhead stream, c) means for condensing and transferring the scrubbed alkylator overhead stream to a finishing reactor having a second alkylation catalyst, as described above, the finishing reactor having a finishing reactor outlet for discharging reacted finishing reactor effluent, d) means for cooling the finishing reactor effluent to a temperature sufficiently low for condensing at least a portion of vaporous aromatic compounds in the catalytic distillation unit; and e) means for directing cooled finishing reactor effluent into the first alkylation catalyst.

In a further embodiment, the apparatus further includes means for removing a substantial portion of any volatile compounds in the finishing reactor effluent before cooling step (d) to form a stripped and cooled finishing reactor effluent. In another embodiment, the first alkylation catalyst comprises at least two lower beds, a lowermost bed, and an uppermost bed. In yet another embodiment, means are provided for directing the stripped and cooled finishing reactor effluent to above at least the two lower beds of the first alkylation catalyst.

Thus, whereas there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

The invention claimed is:

1. A process for the production of alkylated aromatic compounds comprising the steps of:
  a) introducing one or more aromatic compounds and one or more olefins into a catalytic distillation unit having at least two lower beds, a lowermost bed, and an uppermost bed of a first alkylation catalyst, the catalytic distillation unit operated in a combination liquid phase-vapor phase mode under alkylation reaction conditions to produce a liquid alkylator bottoms effluent comprising alkylated aromatic compounds and unreacted aromatic compound discharging below the lowermost bed, and an alkylator vapor overhead stream comprising unreacted aromatic compound and unreacted olefin discharging above the uppermost bed;
  b) condensing the alkylator vapor overhead stream to form a condensed alkylator overhead stream and directing said condensed alkylator overhead stream into a finishing reactor having a second alkylation catalyst and operated in a liquid phase under alkylation reaction conditions wherein the unreacted aromatic compound and unreacted olefin in the alkylator overhead stream are converted to alkylated aromatic compounds with substantially complete consumption of the unreacted olefin, thereby producing a finishing reactor effluent comprising alkylated aromatic compound and essentially no unreacted olefin;
  c) removing a substantial portion of any volatile compounds in the finishing reactor effluent to form a stripped finishing reactor effluent;

d) cooling at least a portion of the finishing reactor effluent to a temperature sufficiently low for condensing at least a portion of vaporous aromatic compounds in the catalytic distillation unit, thereby forming a stripped and cooled finishing reactor effluent; and e) directing said stripped and cooled finishing reactor effluent above at least the two lower beds of the first alkylation catalyst during operation of the catalytic distillation unit; wherein any alkylated aromatic compounds in the alkylator overhead stream are substantially removed prior to the operation of the finishing reactor according to step (b) by use of a suitable absorbent capable of selectively removing alkylated aromatic compounds in the presence of unreacted aromatic compound and unreacted olefin.

2. The process of claim 1, wherein the aromatic compound is benzene.

3. The process of claim 1, wherein the olefin is ethylene or propylene.

4. The process of claim 1, wherein said alkylator bottoms effluent comprises ethylbenzene or cumene.

5. The process of claim 1, wherein said alkylator bottoms effluent further comprises polyalkylated benzenes and unreacted benzene.

6. The process of claim 1, wherein the alkylation reaction conditions of the catalytic distillation unit comprises a pressure of from about 270 psig to about 550 psig and a temperature of from about 185° C. to about 250° C., with an aromatics to olefin weight ratio in the range of about 2.0 to about 3.5.

7. The process according to claim 1, wherein said absorbent is positioned above the uppermost portion of the first alkylation catalyst and below where the alkylator overhead stream is discharged.

8. The process according to claim 1, wherein the first alkylation catalyst comprises a vertical arrangement of two or more baled units of a suitable acidic catalyst having a suitable spacing between each baled catalyst unit.

9. The process according to claim 8, wherein the first alkylation catalyst comprises a vertical arrangement of five to ten baled catalyst units.

10. The process according to claim 9, wherein the first alkylation catalyst comprises a vertical arrangement of seven baled catalyst units.

11. The process according to claim 8, wherein the olefin is fed to the first alkylation catalyst by two to seven split olefin feed lines feeding an equal number of baled catalyst units of a lower portion of a vertical arrangement of three to ten baled catalyst units of the first alkylation catalyst, wherein the number of baled catalyst units is greater than the number of split olefin feed lines, thereby leaving an upper portion of baled catalyst units without olefin feed lines.

12. The process according to claim 8, wherein the olefin is fed to the first alkylation catalyst by three to five split olefin feed lines feeding an equal number of baled catalyst units of a lower portion of a vertical arrangement of four to eight baled catalyst units of the first alkylation catalyst, wherein the number of baled catalyst units is greater than the number of split olefin feed lines, thereby leaving an upper portion of baled catalyst units without olefin feed lines.

13. The process according to claim 1, wherein the aromatic compound is introduced below the lowermost portion of the first alkylation catalyst as a vapor.

14. The process according to claim 1, further comprising (i) condensing the alkylator overhead stream to produce a condensed alkylator overhead stream, and (ii) heating said condensed alkylator overhead stream before introducing the alkylator overhead stream into the finishing reactor.

15. The process according to claim 1, wherein the removing of volatile compounds step (c) is by a lights stripping zone capable of selectively removing gaseous components from the finishing reactor effluent to form a stripped finishing reactor effluent wherein gaseous components have been substantially removed.

16. The process according to claim 15, wherein said lights stripping zone is housed in the uppermost portion of the catalytic distillation unit.

17. The process according to claim 1, wherein the cooling step according to step (c) is effected by one or more coolers or condensers.

18. The process according to claim 1, wherein the cooled finishing reactor effluent is fed via one or more split feed lines to the first alkylation catalyst.

19. The process according to claim 18, wherein the first alkylation catalyst comprises a vertical arrangement of three to ten baled catalyst units and the olefin is fed to the first alkylation catalyst by two to seven split olefin feed lines feeding olefin to an equal number of baled catalyst units in a lower portion of said vertical arrangement of three to ten baled catalyst units of the first alkylation catalyst, wherein the number of baled catalyst units is greater than the number of split olefin feed lines, thereby leaving an upper portion of baled catalyst units without olefin feed lines, wherein cooled finishing reactor effluent is split into a number of split feed lines equal to the number of olefin split lines, each of the split feed lines of cooled finishing reactor effluent injecting into each of the lower portion of baled catalyst units being fed by olefin.

20. The process according to claim 18, wherein the first alkylation catalyst comprises a vertical arrangement of four to eight baled catalyst units and the olefin is fed to the first alkylation catalyst by three to five split olefin feed lines feeding olefin to an equal number of baled catalyst units of a lower portion of said vertical arrangement of four to eight baled catalyst units of the first alkylation catalyst, wherein the number of baled catalyst units is greater than the number of split olefin feed lines, thereby leaving an upper portion of baled catalyst units without olefin feed lines, wherein cooled finishing reactor effluent is split into a number of split feed lines equal to the number of olefin split lines, each of the split feed lines of cooled finishing reactor effluent injecting into each of the lower portion of baled catalyst units being fed by olefin.

21. The process according to claim 1, further comprising processing the alkylator bottoms effluent by a distillation process capable of separating a desired alkylated aromatic compound from other components of the alkylator bottoms effluent.

22. A process for the production of alkylated aromatic compounds comprising the steps of:
  a) introducing one or more aromatic compounds and one or more olefins into a catalytic distillation unit having at least two lower beds, a lowermost bed, and an uppermost bed of a first alkylation catalyst, the catalytic distillation unit operated in a combination liquid phase-vapor phase mode under alkylation reaction conditions to produce a liquid alkylator bottoms effluent comprising alkylated aromatic compounds and unreacted aromatic compound discharging below the lowermost bed and an alkylator vapor overhead stream comprising unreacted aromatic compound and unreacted olefin discharging above the uppermost bed;
  b) substantially removing any alkylated aromatic compounds in the alkylator vapor overhead stream by use of a suitable absorbent capable of selectively removing alkylated aromatic compounds in the presence of unreacted aromatic compound and unreacted olefin, thereby producing a scrubbed alkylator overhead stream;

c) condensing the scrubbed alkylator overhead stream to form a condensed and scrubbed alkylator overhead stream and directing said condensed and scrubbed alkylator overhead stream into a finishing reactor having a second alkylation catalyst and operated in a liquid phase under alkylation reaction conditions wherein the unreacted aromatic compound and unreacted olefin in the scrubbed alkylator overhead stream are converted to alkylated aromatic compounds with substantially complete consumption of the unreacted olefin, thereby producing a finishing reactor effluent comprising alkylated aromatic compound and essentially no unreacted olefin;

d) removing a substantial portion of any volatile compounds in the finishing reactor effluent to form a stripped finishing reactor effluent;

e) cooling at least a portion of the stripped finishing reactor effluent to a temperature sufficiently low for condensing at least a portion of vaporous aromatic compounds in the catalytic distillation unit, thereby forming a stripped and cooled finishing reactor effluent, and f) directing said stripped and cooled finishing reactor effluent above at least the two lower beds of the first alkylation catalyst during operation of the catalytic distillation unit.

23. A process for the production of alkylated aromatic compounds comprising the steps of:

a) introducing one or more aromatic compounds and one or more olefins into a catalytic distillation unit having a first alkylation catalyst comprising a vertical arrangement of three to ten baled catalyst units and having a lowermost baled catalyst unit and an uppermost baled catalyst unit, the catalytic distillation unit operated in a combination liquid phase-vapor phase mode under alkylation reaction conditions to produce a liquid alkylator bottoms effluent comprising alkylated aromatic compounds and unreacted aromatic compound discharging below the lowermost baled catalyst unit and an alkylator vapor overhead stream comprising unreacted aromatic compound and unreacted olefin discharging above the uppermost baled catalyst unit, wherein olefin is fed to the first alkylation catalyst by two to seven split olefin feed lines feeding an equal number of baled catalyst units of a lower portion of said vertical arrangement of three to ten baled catalyst units, wherein the number of baled catalyst units is greater than the number of split olefin feed lines, thereby leaving an upper portion of baled catalyst units without olefin feed lines;

b) substantially removing any alkylated aromatic compounds in the alkylator overhead stream by use of a suitable absorbent capable of selectively removing alkylated aromatic compounds in the presence of unreacted aromatic compound and unreacted olefin, thereby producing a scrubbed alkylator overhead stream;

c) condensing the scrubbed alkylator overhead stream to form a condensed and scrubbed alkylator overhead stream and directing said condensed and scrubbed alkylator overhead stream into a finishing reactor having a second alkylation catalyst and operated in a liquid phase under alkylation reaction conditions wherein the unreacted aromatic compound and unreacted olefin in the scrubbed alkylator overhead stream are converted to alkylated aromatic compounds with substantially complete consumption of the unreacted olefin, thereby producing a finishing reactor effluent comprising alkylated aromatic compound and essentially no unreacted olefin;

d) removing a substantial portion of any volatile compounds in the finishing reactor effluent to form a stripped finishing reactor effluent;

e) cooling at least a portion of the stripped finishing reactor effluent to a temperature sufficiently low for condensing at least a portion of vaporous aromatic compounds in the catalytic distillation unit, thereby forming a stripped and cooled finishing reactor effluent, and f) directing said stripped and cooled finishing reactor effluent to the first alkylation catalyst during operation of the catalytic distillation unit, wherein cooled finishing reactor effluent is split into a number of split feed lines equal to or greater than the number of olefin split lines, each of the split feed lines of cooled finishing reactor effluent injecting above each of the lower portion of baled catalyst units being fed by olefin.

24. The process according to claim 23, wherein olefin partial pressures throughout the lower portion of baled catalyst units do not vary by more than about five percent.

* * * * *

UNITED STATES PATENT AND TRADEMARK OFFICE
CERTIFICATE OF CORRECTION

PATENT NO. : 7,632,974 B2  Page 1 of 1
APPLICATION NO. : 11/489017
DATED : December 15, 2009
INVENTOR(S) : Kevin J. Schwint It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 694 days.

Signed and Sealed this

Second Day of November, 2010

David J. Kappos
*Director of the United States Patent and Trademark Office*